(12) United States Patent
Shetty

(10) Patent No.: US 8,835,507 B2
(45) Date of Patent: Sep. 16, 2014

(54) ADAMANTANE DERIVATIVES POSSESSING ANTI-VIRAL AND ANTI-MICROBIAL ACTIVITY

(71) Applicant: B. Vithal Shetty, Germantown, MD (US)

(72) Inventor: B. Vithal Shetty, Germantown, MD (US)

(73) Assignee: Vymed Corporation, Germantown, MD (US)

( * ) Notice: Subject to any disclaimer, the term of this patent is extended or adjusted under 35 U.S.C. 154(b) by 10 days.

(21) Appl. No.: 13/768,316

(22) Filed: Feb. 15, 2013

(65) Prior Publication Data

US 2013/0231391 A1 Sep. 5, 2013

Related U.S. Application Data

(60) Provisional application No. 61/601,105, filed on Feb. 21, 2012.

(51) Int. Cl.
| | | |
|---|---|---|
| *A61K 31/13* | (2006.01) | |
| *C07C 211/38* | (2006.01) | |
| *C07C 239/04* | (2006.01) | |

(52) U.S. Cl.
CPC ........... *C07C 239/04* (2013.01); *C07C 2103/74* (2013.01); *C07C 211/38* (2013.01)
USPC ............................ 514/662; 514/612; 514/659

(58) Field of Classification Search
CPC .. C07C 2103/74; C07C 211/38; C07C 239/04
USPC ............................ 514/612, 662; 564/117, 459
See application file for complete search history.

(56) References Cited

U.S. PATENT DOCUMENTS 6,384,083 B1 * 5/2002 Ludwig et al. ................. 514/662
7,456,222 B2 * 11/2008 Protopopova et al. ......... 514/648

* cited by examiner

*Primary Examiner* — My-Chau T Tran
(74) *Attorney, Agent, or Firm* — Karta Law Firm, LLC; Glenn E. Karta

(57) ABSTRACT

The present invention relates to adamantane derivatives that are active as antiviral and anti-microbial agents; antiviral or antibacterial compositions comprising adamantane derivatives or pharmaceutically acceptable salts thereof; and methods of preventing or treating viral or bacterial infections in mammalian hosts through the administration of adamantine derivatives or their salts or pharmaceutical compositions comprising the same. In particular, viral infections prevented or treated by the methods of the present invention may include, but are not limited to, those caused by arenavirus or one or more pox viruses, such as vaccinia and/or variola.

10 Claims, No Drawings

ADAMANTANE DERIVATIVES POSSESSING ANTI-VIRAL AND ANTI-MICROBIAL ACTIVITY

CROSS-REFERENCE TO RELATED APPLICATIONS

This application is related to and claims priority under 35 U.S.C. §119(e) to U.S. Provisional Application No. 61/601,105, filed Feb. 21, 2012 and incorporated by reference in its entirety herein.

STATEMENT REGARDING FEDERALLY SPONSORED RESEARCH

Not applicable

BACKGROUND OF THE INVENTION

1. Technical Field

The present invention relates to adamantane derivatives that are active as antiviral and anti-microbial agents against various organisms listed by the Centers for Disease Control as Category A, B and C pathogens. These compounds have been shown to be particularly active against the vaccinia virus.

2. Description of the Background Art

Adamantane, or tricyclo[3.3.1.13.7]decane, is a cycloalkane consisting of four cyclohexane rings arranged in an armchair configuration. Because of its symmetry, rigidity and stable structure, it is known as a desirable component for use in pharmaceutical compositions. Additionally, adamantane derivatives and resins have been investigated for use in optics, electronics and dental composites.

Adamantane derivatives are well known to have anti-viral and anti-microbial activity. Amantidine, believed to have been the first adamantane derivative to be used medicinally, is an adamantine that was modified by the addition of an amino group. It has been used primarily to combat various strains of influenza. Additional adamantane derivatives have been described. See generally U.S. Pat. No. 4,661,512. Adamantane derivatives have been used therapeutically in the treatment or prevention of Parkinson's disease, Borna disease, HIV1 and complications associated with diabetes, such as high intraocular eye pressure. Adamantane's mode of action remains largely unknown.

It has now been found that the adamantane derivatives disclosed herein have unexpectedly improved properties compared to other antiviral and antimicrobial agents. Specifically, the adamantine derivatives described herein have been shown to be active against the vaccinia virus, as well as other microorganisms classified by the National Institute of Allergy and Infectious Diseases as Category A, B and C pathogens. Vaccinia virus is associated with smallpox, which the Department of Homeland Security has designated a "material threat" to our national security. Thus, there is a need for agents that are effective at preventing or treating vaccinia related infections.

SUMMARY OF THE INVENTION

In one aspect, the present invention relates to a compound, or pharmaceutically acceptable salts thereof, having the following structure:

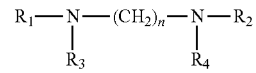

wherein R1 and R2 independently comprise 1-adamantane, 2-adamantane or noradamantane;

R3 and R4 independently comprise hydrogen, halogen or a low MW alkyl;

and n represents a number from 1 to 6.

In another aspect, the present invention relates to an antiviral composition which comprises:

(a) an effective amount of a compound described above; and (b) a pharmaceutically acceptable carrier.

In another aspect, the present invention relates to an antibacterial composition which comprises:

(a) an effective amount of a compound described above; and (b) a pharmaceutically acceptable carrier.

In another aspect, the present invention relates to an antiviral and antibacterial composition which comprises:

(a) an effective amount of a compound described above; and (b) a pharmaceutically acceptable carrier.

In another aspect, the present invention relates to a method for preventing or treating a bacterial infection in a mammalian host, said method comprising administering to a mammal in need thereof an effective amount of a compound described above.

In another aspect, the present invention relates to a method for preventing or treating a viral infection in a mammalian host, said method comprising administering to mammal in need thereof an effective amount of a compound described above.

In another aspect, the present invention relates to a method for preventing or treating a viral infection wherein the viral infection is caused by vaccinia or variola virus, said method comprising administering to a mammal in need thereof an effective amount of a compound described above.

DETAILED DESCRIPTION OF THE PREFERRED EMBODIMENTS

The present invention encompasses compounds having the formula depicted and described above. Within the scope of the present invention are also pharmaceutical compounds and compositions that contain the claimed adamantane derivative. The present invention also encompasses combinations of the adamantane derivative with other desirable active ingredients and suitable pharmaceutically effective carriers. The present invention also encompasses methods of preventing or treating a viral or bacterial infection in a mammalian host through the administration of a pharmaceutically effective amount of the adamantane derivative.

Example 1

One preferred embodiment of the present invention, designated Compound 6, may be synthesized according to the following reaction scheme:

Step A. Preparation of Intermediate Compound 3.

Compound 3 is synthesized by dissolving 20 g of 1-adamantane amine, Compound 1, in 800 ml of absolute methanol in a two liter flask. To the clear solution, and with continued stirring, 10 ml of 40% glyoxal in 80 ml absolute methanol is added all at once. The solution was stirred continuously for 34 hours. The solution was cooled in an ice bath and the solid was removed by filtration and dried. The final yield and melting point for the product of Step A:
WT: 19.9 g
m.p: 243-245° C.

Step B. Preparation of Compound 6.

Compound 4 was synthesized by placing 3 g of Compound 3 obtained in Step A in a 500 ml flask with 170 ml of absolute ethanol. The solution was stirred under a blanket of nitrogen until clear. Then the flask was connected to a balloon containing hydrogen and stirring was continued for 24 hours under hydrogen and nitrogen. The solution was filtered and concentrated under vacuum. The solid, Compound 4, was dissolved in methanol and filtered. The solution was made acidic with concentrated hydrochloric acid, cooled, and the solid collected by filtration. The solid was dissolved in hot methanol. Charcoal was added and the solution was filtered. The solid, Compound 5, was dissolved in boiling water, cooled, and made basic using 20% sodium hydroxide. The base was mixed with water and acidified with methane sulfonic acid, cooled and the salt removed by filtration. The solid was recrystallized from boiling methanol to obtain Compound 6. The final yield and melting point for the product of Step B:
WT: 0.6 g
m.p.: >310°

Analysis Calculations for Compound 6:

| $C_{24}H_{44}N_2S_2O_6$ (520.74) | % Calculated | % Found |
|---|---|---|
| C | 55.35 | 54.07 |
| H | 8.51 | 8.46 |
| N | 5.57 | 5.15 |
| S | 12.19 | 12.05 |
| O | 18.43 | |

The product of the above reaction scheme, Compound 6, was found to have the following structure:

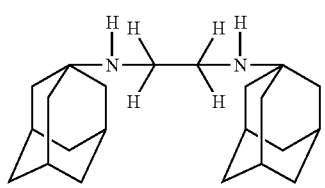

Example 2

Another preferred embodiment of the present invention, designated Compound 7, may be synthesized according to the following scheme.

Step A. Preparation of Compound 7.

In a 500 ml flask, 5% sodium hypochlorite solution was added and cooled to 10° C. While stirring, 1.5 g of Compound 4 (described in Example 1) was added all at once. This solution was stirred continuously for 22 hours. The resulting yellowish solid was removed by filtration and washed with water. It was recrystallized using boiling acetonitrile, filtered while hot and allowed to cool in an ice bath. The resulting slightly yellowish solid was removed by filtration and dried.
WT: 0.5 g
m.p.: 140-142° C.

Analysis Calculations for Compound 7:

| $C_{22}H_{34}N_2Cl_2$ | % Calculated | % Found |
|---|---|---|
| C | 66.43 | 66.50 |
| H | 8.62 | 8.67 |
| N | 7.04 | 7.02 |
| Cl | 17.84 | 17.78 |

The product of the above reaction scheme, Compound 7, was found to have the following structure:

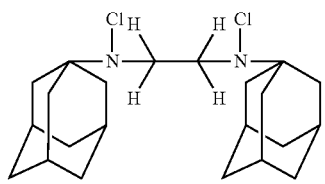 [SMILES: C(CNC12CC3CC(CC(C3)C1)C2)NC12CC3CC(CC(C3)C1)C2]

Testing of Compounds 6 and 7 for Antiviral and Antimicrobial Activity.

Test A.

Representative compounds of the present invention, Compound 6 and Compound 7, were screened against Vaccinia virus, WR strain, to test for antiviral activity. The results are tabulated below:

TABLE 1

| Compound Identification | IC50 (ug/ml) | TC50 (ug/ml) | Therapeutic Index | Comments |
|---|---|---|---|---|
| Ribivirin | 27.90 | >100 | >3.5 | Moderate |
| Cidofir | NA | >100 | NA | Inactive |
| Compound 7 | 6.37 | 63.40 | 9.96 | Moderate |
| Compound 6 | 0.32 | 5.58 | 17.45 | Active |

As indicated in Table 1, of the compounds screened, Compound 6 and Compound 7 showed moderate to high activity against vaccinia virus. The levels of activity observed for these two isolates are significantly greater than the levels observed using the control compounds ribivirin and cidofir.

Test B.

Compound 6 was evaluated to test anti-microbial activity against anthrax, *E. coli* and the plague. The results are tabulated below and the data presented in the form of MIC values.

TABLE 2

| Strain | MIC (ug/ml) |
|---|---|
| anthrax | 1-4 |
| *E. coli* | 4-8 |
| plague | 4 |

Test C.

Compound 6 was evaluated to test anti-microbial activity against several common strains of bacteria known to cause infection in humans and/or other animals. The results are tabulated below and the data presented in the form of MIC values.

TABLE 3

| Strain | MIC (ug/ml) |
|---|---|
| *B. anthracis* (Ames)(CAMHB) | 0.25 |
| *Y. pestis* (CO92)(CAMHB) | ≤0.06 |

TABLE 3-continued

| Strain | MIC (ug/ml) |
|---|---|
| B. mallei (ATCC 23344)(CAMHB) | 2 |
| B. pseudomallei (ATCC 23342)(CAMHB) | 2 |
| F. tularensis (SCHU4)(CAMHB + IV) | ≦0.06 |
| S. aureus (ATCC 29213)(CAMHB + IV) | 1 |
| E. coli (ATCC 25922)(CAMHB) | ≦0.06 |
| E. coli (ATCC 25922)(CAMHB + IV) | ≦0.06 |
| P. aeruginosa (ATCC 27853)(CAMHB) | 2 |
| P. aeruginosa (ATCC 27853)(CAMHB + IV) | 4 |

Test D.

Additional testing was carried out by screening Compound 6 and Compound 7 against the arenaviruses Tacaribe and Pichinde. The results show that the compounds of the present invention were moderately active against both the Tacaribe and the Pichinde virus. The results are tabulated below.

TABLE 4

| Compound | Virus | EC50 | IC50 | SI |
|---|---|---|---|---|
| Compound 6 | Tacaribe | 1.1 | 6 | 5 |
|  | Pichinde | 21 | 11 | 1 |
| Compound 7 | Tacaribe | 1 | 17 | 17 |
|  | Pichinde | >32 | 3.4 | 0 |

As noted above, compounds within the present invention have antiviral and antimicrobial activity and thus may be administered to patients in need thereof. For therapeutic or prophylactic treatment, the compounds of the present invention may be formulated in a pharmaceutical composition, which may include, in addition to an effective amount of the compound of the present invention, pharmaceutically acceptable carriers, thickeners, fillers, diluents, buffers, enhancers, preservatives, surface active agents and the like. Pharmaceutical compositions may also include one or more other active ingredients if necessary or desirable.

The pharmaceutical compositions of the present invention may be administered in a number of ways as will be apparent to one of ordinary skill in the art. Administration may be performed topically, orally (including buccal and sublingual), rectally, nasally, vaginally, by inhalation, or parenterally (including subcutaneous, intramuscular, intravenous and intradermal), for example.

Topical administration may be performed using formulations of the compound of the present invention that may include ointments, lotions, creams, gels, drops, suppositories, sprays, liquids and powders. Oral formulations include powders, granules, suspensions or solutions in water or non-aqueous media, capsules or tablets, for example. Thickeners, flavorings, diluents, emulsifiers, dispersing aids or binders may be used as needed.

Parenteral formulations may include sterile aqueous solutions which may also contain buffers, diluents and other suitable additives.

The dose regimen will depend on a number of factors which may readily be determined by one of ordinary skill, such as severity and responsiveness of the condition to be treated, but will normally be one or more doses per day, with a course of treatment lasting from several days to several months, or until a cure is effected or a diminution of disease state is achieved. One of ordinary skill may readily determine optimum dosages, dosing methodologies and repetition rates. In general, it is contemplated that unit dosage form compositions according to the present invention will contain from about 0.01 mg to about 500 mg of active ingredient, preferably about 0.1 mg to about 10 mg of active ingredient. Topical formulations (such as creams, lotions, solutions, etc.) may have a concentration of active ingredient of from about 0.1% to about 50%, preferably from about 0.1% to about 10%. However, final strength of the finished dosage form will depend on the factors listed above and may be readily determined by one of ordinary skill.

What is claimed:

1. A compound derivative, or pharmaceutically acceptable salt thereof, represented by the following general formula:

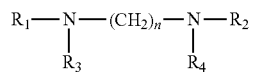

wherein R1 and R2 independently comprise 1-adamantane, 2-adamantane or noradamantane;
wherein R3 and R4 independently comprise hydrogen, halogen or a low MW alkyl;
and wherein n represents a number from 1 to 6.

2. An antiviral composition which comprises:
(a) an effective amount of a compound of claim 1; and
(b) a pharmaceutically acceptable carrier.

3. An antibacterial composition which comprises:
(a) an effective amount of a compound of claim 1; and
(b) a pharmaceutically acceptable carrier.

4. An antiviral and antibacterial composition which comprises:
(a) an effective amount of a compound of claim 1; and
(b) a pharmaceutically acceptable carrier.

5. A method for preventing or treating a bacterial infection in a mammalian host, said method comprising administering to a mammal in need thereof an effective amount of a compound of claim 1.

6. A method for preventing or treating a viral infection in a mammalian host, said method comprising administering to a mammal in need thereof an effective amount of a compound of claim 1.

7. A method for preventing or treating a viral infection in a mammalian host, wherein said viral infection is caused by vaccinia virus, said method comprising administering to a mammal in need thereof an effective amount of a compound of claim 1.

8. A method for preventing or treating a viral infection in a mammalian host, wherein said viral infection is caused by variola virus, said method comprising administering to a mammal in need thereof an effective amount of a compound of claim 1.

9. A method for preventing or treating a viral infection in a mammalian host, wherein said viral infection is caused by an arenavirus, and wherein said method comprising administering to a mammal in need thereof an effective amount of a compound of claim 1.

10. A compound according to claim 1, wherein $R_1$ and $R_2$ are 1-adamantane; $R_3$ and $R_4$ are hydrogen; and n is 2.

* * * * *